United States Patent [19]
Reber et al.

[11] Patent Number: 5,980,934
[45] Date of Patent: Nov. 9, 1999

[54] TRANSDERMAL DELIVERY APPARATUS

[75] Inventors: William L. Reber, Schaumburg; Jeffrey G. Toler, Algonquin, both of Ill.; Cary D. Perttunen, Shelby Township, Mich.

[73] Assignee: Motorola, Inc., Schaumburg, Ill.

[21] Appl. No.: 08/858,677

[22] Filed: May 19, 1997

[51] Int. Cl.⁶ .................................................. A61F 13/00
[52] U.S. Cl. .......................... 424/449; 424/443; 424/447
[58] Field of Search ................................ 424/443, 447, 424/449

[56] References Cited

U.S. PATENT DOCUMENTS

| | | | |
|---|---|---|---|
| 4,767,402 | 8/1988 | Kost et al. | 604/22 |
| 4,780,212 | 10/1988 | Kost et al. | 604/22 |
| 4,948,587 | 8/1990 | Kost et al. | 424/435 |
| 5,074,977 | 12/1991 | Cheung et al. | 204/153.1 |
| 5,580,794 | 12/1996 | Allen | 436/169 |
| 5,597,182 | 1/1997 | Reber et al. | 283/67 |
| 5,714,123 | 2/1998 | Sohrab | 422/99 |
| 5,728,352 | 3/1998 | Poto et al. | 422/82.05 |
| 5,746,711 | 5/1998 | Sibalis et al. | 604/20 |

*Primary Examiner*—Jose' G. Dees
*Assistant Examiner*—Kathryne E. Shelborne
*Attorney, Agent, or Firm*—Jeffrey G. Toler; James E. Gauger

[57] ABSTRACT

In accordance with a first aspect, a noninvasive apparatus comprises a card-shaped housing which supports the transdermal delivery device (10). In accordance with a second aspect, a retaining member (18) retains a removable member (16) proximate to at least a portion of the transdermal delivery device (10). In accordance with a third aspect, a transdermal delivery apparatus comprises a processor (24) to receive delivery data via an interface (28) and to direct a transdermal delivery device (10) based upon the delivery data.

26 Claims, 5 Drawing Sheets

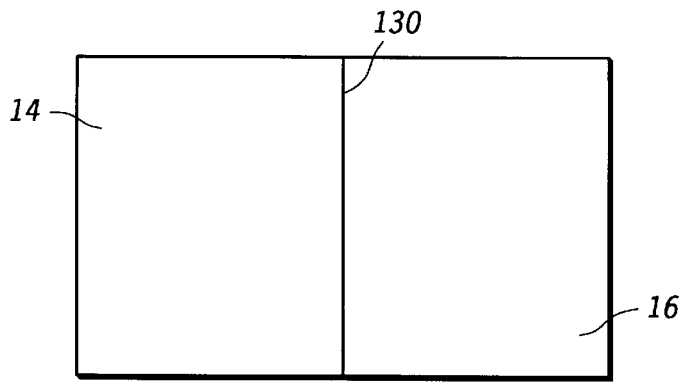
*FIG.6*
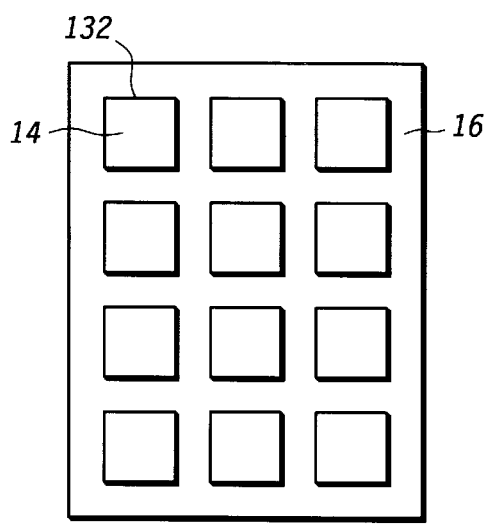 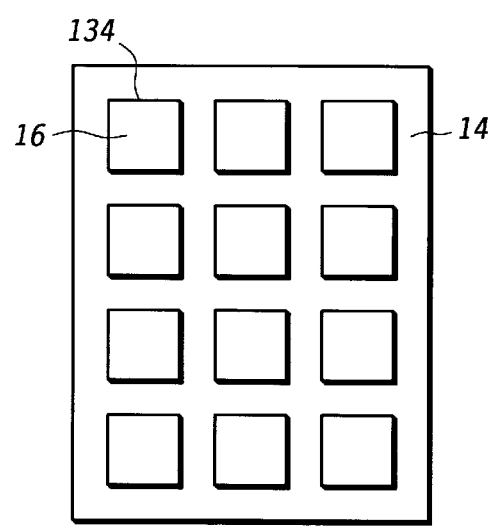
*FIG.7* *FIG.8*

TRANSDERMAL DELIVERY APPARATUS

CROSS REFERENCE TO RELATED APPLICATIONS

The present application is a continuation in part of the following application which is assigned to the same assignee as the present application:

Noninvasive apparatus, having U.S. Ser. No. 08/833,566 filed Apr. 7, 1997.

The present application is also related to the following application which is assigned to the same assignee as the present application:

Medical Communication Apparatus, System, and Method, having U.S. Ser. No. 08/811,081, filed Mar. 3, 1997.

The subject matter of the above-identified related applications is hereby incorporated by reference into the disclosure of this application.

TECHNICAL FIELD

The present invention relates to transdermal drug delivery systems.

BACKGROUND OF THE INVENTION

Recent efforts have been directed in the field of drug delivery by transdermal and transbuccal permeation. Using transdermal permeation or percutaneous absorption, a substance such as a drug is noninvasively delivered into an individual's bloodstream through his/her various layers of skin. Using transbuccal permeation, a substance is noninvasively delivered into an individual's bloodstream through a buccal membrane.

A transdermal patch, such as a nicotine patch, is an example of a transdermal drug delivery device. Transdermal patches are typically adhered to an individual's arm to deliver a drug into his/her bloodstream. Typically, each transdermal patch is dedicated for a single drug delivery application. For example, a nicotine patch is dedicated to deliver nicotine for a smoking cessation application.

BRIEF DESCRIPTION OF THE DRAWINGS

The invention is pointed out with particularity in the appended claims. However, other features of the invention are described in the following detailed description in conjunction with the accompanying drawings in which:

FIG. 6 is a view of a first alternative configuration of the transducer and the member for embodiments of the present invention;

FIG. 7 is a view of a second alternative configuration of the transducer and the member for embodiments of the present invention; and FIG. 8 is a view of a third alternative configuration of the transducer and the member for embodiments of the present invention.

DETAILED DESCRIPTION OF A PREFERRED EMBODIMENT

Figure 1:
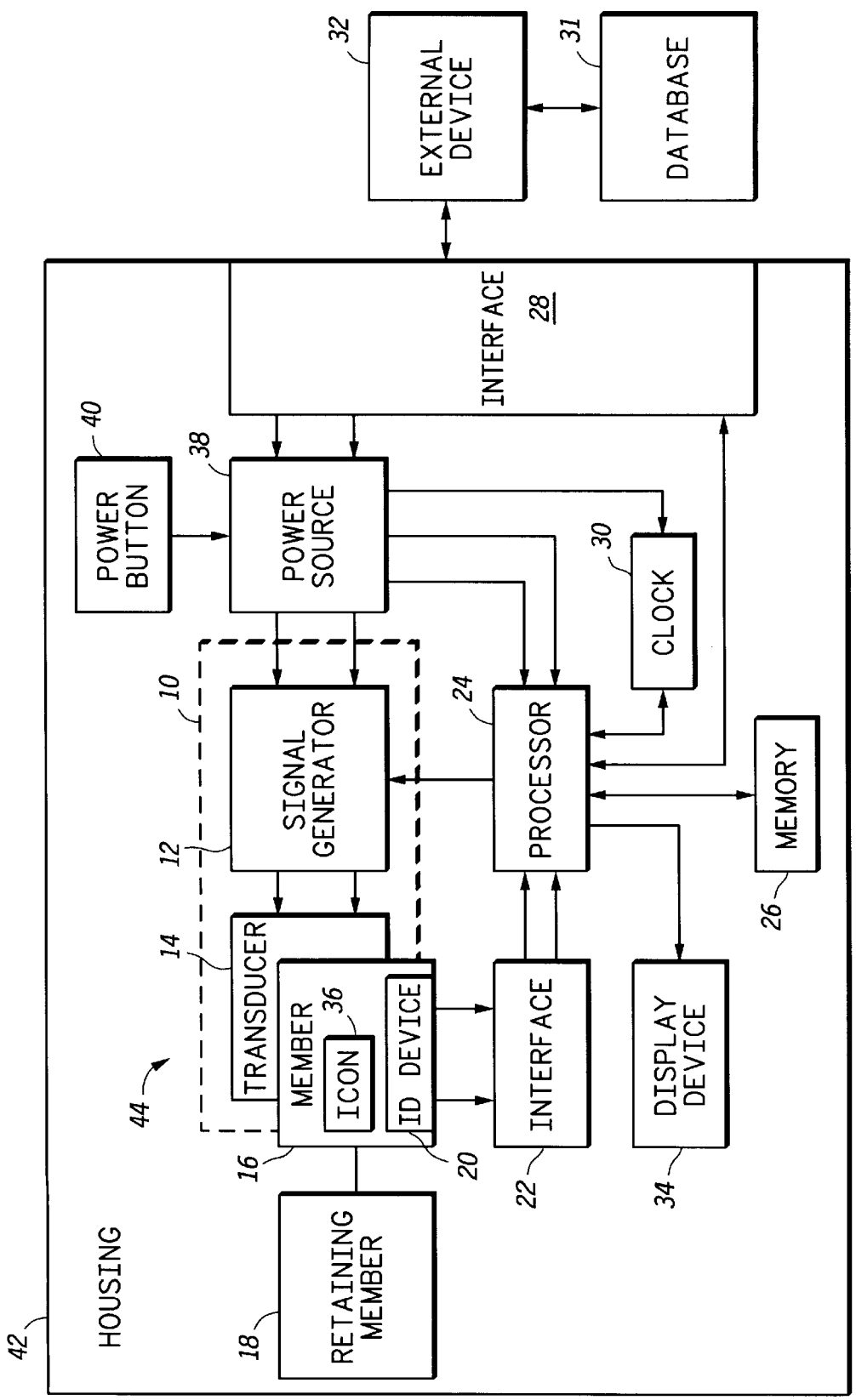
FIG. 1 is a block diagram of a transdermal delivery apparatus in accordance with the present invention.

FIG. 1 is a block diagram of a transdermal delivery apparatus in accordance with the present invention. The apparatus includes a transdermal delivery device 10 to facilitate transdermal delivery of a substance to an end user. Examples of the substance include, but are not limited to, therapeutic substances, pharmaceutical substances, medicines, drugs, antigens, vitamins, proteins, hormones such as insulin, organic compounds and inorganic compounds.

Preferably, the transdermal delivery device 10 delivers the substance through the skin of the end user by transdermal permeation or percutaneous absorption. Alternatively, the transdermal delivery device 10 can delivery the substance through a buccal membrane by transbuccal permeation. Regardless of where the substance is delivered, the transdermal delivery device 10 delivers the substance without penetrating the skin or another portion of the end user's body.

Preferably, the transdermal delivery device 10 includes a signal generator 12 and a transducer 14. The signal generator 12 drives the transducer 14 to produce acoustic pressure waves. The acoustic pressure waves enhance and control the permeation of the substance from outside of the end user's skin through its various layers into the bloodstream.

In accordance with the teachings in U.S. Pat. Nos. 4,767,402, 4,780,212, 4,948,587 which are hereby incorporated by reference into this disclosure, it is preferred that the transducer 14 includes an ultrasonic emitter. In this case, the ultrasonic emitter emits an ultrasonic signal having a frequency between 20 kHz and 10 MHz, with a preferred range being between 0.5 MHz and 1.5 MHz. Further, the intensity of the ultrasound signal is selected so as not to burn the end user. In general, the ultrasonic emitter can emit either a pulsed or a continuous ultrasonic signal.

The apparatus further comprises a member 16 which supports the substance to be transdermally delivered. Preferably, the member 16 is adjacent at least a portion of the transdermal delivery device 10. In this case, it is further preferred that the member 16 covers at least a portion of the transdermal delivery device 10, such as at least a portion of the transducer 14. Alternatively, the apparatus can include a substance handling conduit to communicate the substance from the member 16 to the transdermal delivery device 10. In a preferred embodiment, the member 16 has the form of a pad which is placed over at least a portion of the transdermal delivery device 10.

The member 16 can be permanently integrated with the apparatus or can be removable. If removable, the member 16 is retained by a retaining member 18. The retaining member 18 retains the member 16 proximate to at least a portion of the transdermal delivery device 10.

Preferably, the member 16 includes an identifier device 20 to identify the substance supported thereby. The identifier device 20 can include an electronic component having a parameter which identifies the substance. In this case, for example, the identifier device 20 can include a resistor having a resistance which uniquely identifies the substance. Alternatively, the identifier device 20 can include a machine-readable storage medium to store machine-readable data indicative of the substance. In this case, the machine-readable storage medium can include an optical storage medium to store optical data, a magnetic storage medium to store magnetic data, or an electronic storage medium (e.g. a memory) to store electronic data.

The apparatus includes an interface 22 to communicate with the member 16. The interface 22 includes a plurality of electrodes which either capacitively, inductively, or directly couple to the member 16. Preferably, the interface 22 includes electrodes to couple with the identifier device 20. Via the interface 22, a processor 24 determines the transdermally-deliverable substance supported by the member 16.

The processor 24 directs operation of the transdermal delivery device 10 based upon delivery data stored in a memory 26 and/or received via an interface 28. Preferably, the delivery data includes substance-identification data to identify which substance is to be delivered, dosage data indicating a dosage of the substance to be delivered, and delivery times at which the substance is to be delivered.

The processor 24 directs activation and deactivation of the transdermal delivery device 10 based upon the substance-identification data, the dosage data, and the delivery times. In particular, the processor 24 inhibits activation of the transdermal delivery device 10 if the substance supported by the member 16 differs from a substance encoded by the substance-identification data. This is beneficial in preventing delivery of an inappropriate substance, for example, if an inappropriate substance-supporting member is applied to the apparatus.

Additionally, the processor 24 can disable transdermal delivery based upon the delivery times and a time signal from a clock 30. In this case, the processor 24 can inhibit activation of the transdermal delivery device 10 if the clock 30 indicates a time prior to or beyond a predetermined delivery period. This is beneficial in preventing substance delivery at undesirable times of day, and preventing an excessive number of deliveries during a day.

If the identifier device 20 indicates the desired substance and the clock 30 indicates a time within a delivery period, the processor 24 activates the transdermal delivery device 10. In dependence upon the dosage data, the processor 24 controls parameters of the transdermal delivery device 10 including the frequency, intensity, and duration of the signal emitted by the transducer 14.

Upon delivering the substance, the processor 24 writes compliance data to the memory 26 and/or to the interface 28. The compliance data can include a time and date at which the substance is delivered, a name or an identifier of the substance, and a dosage of the substance. If the substance is not delivered during a delivery period, the processor 24 optionally writes data indicating an instance of noncompliance to the memory 26 and/or to the interface 28. The noncompliance data can include a time and date of noncompliance.

As a result, a compliance history is maintained either locally in the memory 26 or externally in a database 31 associated with an external device 32 in communication with the interface 28. The transdermal delivery apparatus and the database 31 can monitor compliance and noncompliance in accordance with the teachings in the aforementioned patent application "Medical Communication Apparatus, System, and Method", U.S. Ser. No. 08/811,081.

The external device 32 can have various forms. Of particular interest is where the external device 32 includes a computer or a like processing apparatus. In this case, the external device 32 can include a desktop computer, a laptop computer, a palmtop computer, or a personal digital assistant. Alternatively, the external device 32 can include a communication device such as a two-way pager, a telephone, a cellular telephone, or a personal communication system (PCS) telephone. As another alternative, the external device 32 can include a base station or other transceiver in a communication network such as a paging network, a wireless telephone network, a wireless data network, or a satellite network.

Dependent upon the external device 32, the interface 28 can include any of: (i) a PCMCIA interface for mating in a PCMCIA slot; (ii) a serial interface for mating with a serial port; (iii) a parallel interface for mating with a parallel port; (iv) a SCSI interface for mating with a SCSI port; (v) an infrared interface for communicating with an infrared port; (vi) a radio frequency transceiver for communicating with a radio frequency port; (vii) a telephone interface for mating with a telephone port; (viii) an interface for mating with a data port in a wireless telephone; or (ix) a smart card interface. In general, the interface 28 can include any plurality of connectors which mate with a plurality of connectors associated with the external device 32. Additionally, any signal standard can be used to communicate signals between the apparatus and the external device 32.

Optionally, the apparatus includes a display device 34 responsive to the processor 24. The display device 34 displays human-readable textual and/or graphical information associated with the delivery data. The information can include information to alert an end user of a time to transdermally receive a substance, and information indicating which substance is to be delivered. To indicate which substance is to be delivered, the display device 34 can display textual information such as "insulin", or can display graphical information such as an icon corresponding to an icon 36 associated with the member 16. The icon 36 can be supported by the member 16 or by packaging associated with the member 16.

Generally, the display device 34 can include a plurality of liquid crystal display (LCD) elements or a plurality of light-emitting display (LED) elements to display the information. The display elements can be arranged as an array of pixels or as segments in a segmented display (e.g. a seven-segment display).

The various components of the apparatus are selectively powered by a power source 38. The power source 38 can include battery-receiving terminals in contact with a battery. Alternatively, the power source 38 can include a solar cell. As another alternative, the power source 38 can include a plastic battery. Optionally, the external device 32 can power the various components of the apparatus and/or recharge the battery in the power source 38 via the interface 28.

In response to a first user-initiated input received by a power button 40, the power source 38 powers various components to activate the apparatus. In response to a second user-initiated input received by the power button 40, the power source 38 unpowers various components to deactivate the apparatus.

The apparatus includes a housing 42 to house and/or support the transdermal delivery device 10, the member 16, the retaining member 18, the interface 22, the processor 24, the memory 26, the interface 28, the clock 30, the display device 34, the power source 38, and the power button 40. Preferably, the housing 42 is sized to be handheld by the end user. It is further preferred that the housing 42 be sized and shaped for carrying within a wallet, a purse, or a pocket of the end user. For these purposes, it is preferred that the housing 42 be card shaped. In this case, the housing 42 can have the size of a credit card, a PCMCIA card, a business card, a smart card, an index card, a trading card, or a playing card, for example.

It is also preferred that the housing 42 be either rigid, semi-rigid, or resilient. The housing 42 can be resilient to deform over a portion of the end user's body when in use, and to recover its shape after use.

Optionally, the housing 42 includes a grasping region 44 for grasping by a hand of the end user. In this case, the transdermal delivery device 10 delivers the substance to a portion of the hand which grasps the grasping region 44. For this purpose, the transducer 14 and the member 16 can be located proximate to the grasping region 44. The portion of the hand to which the substance is delivered can include the thumb, the fingers, the palm, or the back of the hand. In general, however, the transdermal delivery device 10 can deliver the substance to any portion of the end user's body including but not limited to his/her arms, legs, and feet.

As another option, the apparatus can include a temperature control element such as a heating element or a cooling element. The temperature control element maintains the substance supported by the member 16 within a predetermined temperature range. Preferably, the temperature control element includes a thermoelectric cooling member to draw heat from the substance while the member 16 is retained by the retaining member 18. The thermoelectric cooling member actively draws heat in response to an electrical signal applied thereto.

The predetermined temperature range can differ from substance to substance. In this case, the predetermined temperature range can be dictated by the identifier device 20 and/or by the delivery data.

Figure 2:
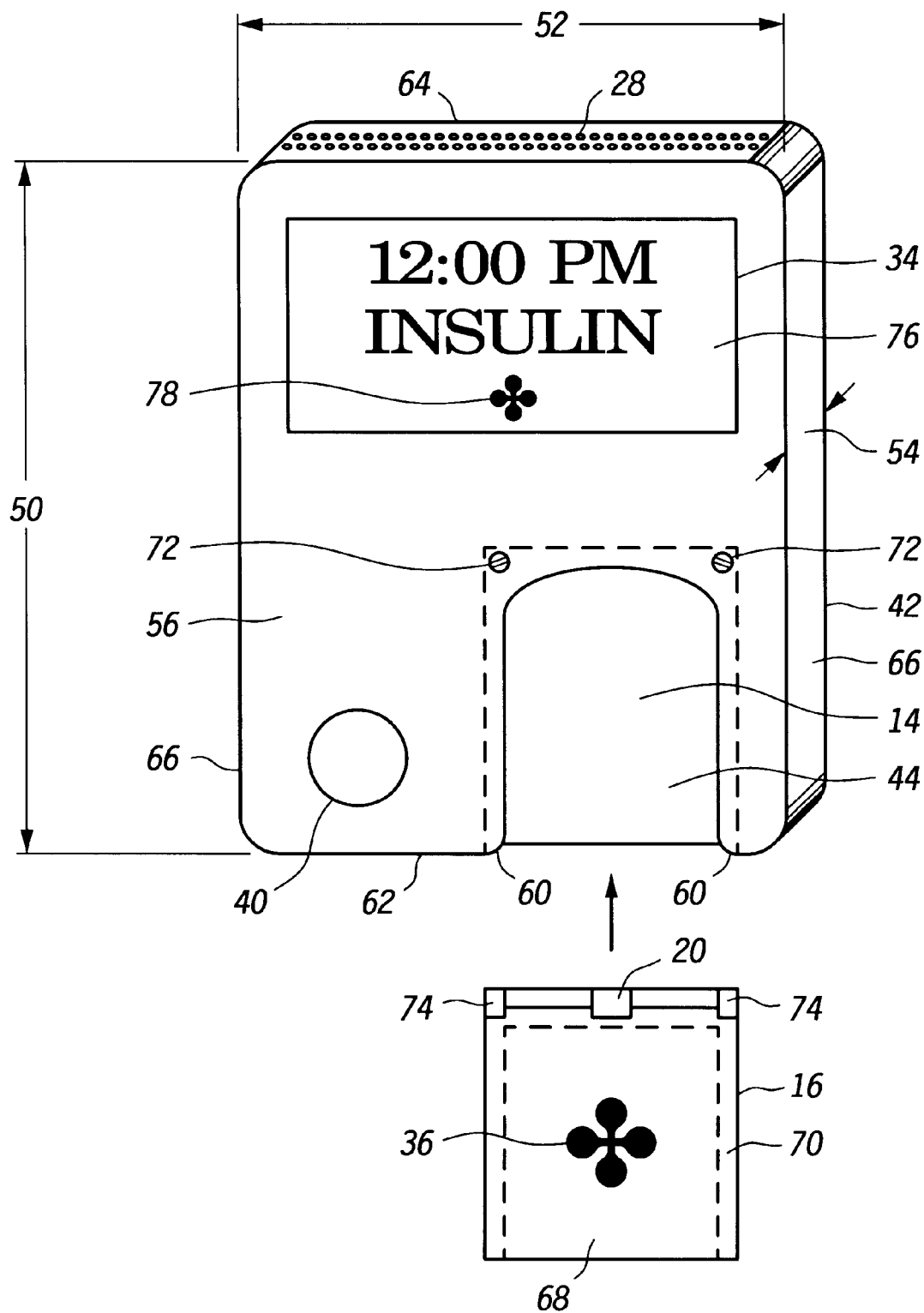
FIG. 2 is a view of a first embodiment of a transdermal delivery apparatus in accordance with the present invention.

FIG. 2 is a view of a first embodiment of a transdermal delivery apparatus in accordance with the present invention. In this embodiment, the housing 42 is card-shaped. The housing 42 is shaped and sized in accordance with a PCMCIA (Personal Computer Memory Card International Association) form standard. The housing 42 has a length 50 of 85.6 mm and a width 52 of 54 mm. The housing 42 has a thickness 54 dependent upon the PCMCIA type. For example, the thickness 54 is 3.3 mm for Type I, 5.0 mm for Type II, and 10.5 mm for Type III. Preferably, the housing 42 is rigid or semi-rigid.

The interface 28 comprises a PCMCIA bus connector. In accordance with PCMCIA standards, the interface 28 includes sixty-eight connectors which mate with sixty-eight pins in a mating connector associated with the external device 32. Typically, the external device 32 includes a socket into which the apparatus is inserted to mate the interface 28 thereto. Signals are communicated via the interface 28 in accordance with PCMCIA signal standards.

The housing 42 has a face 56 at which the display device 34 is viewable and at which the grasping region 44 is disposed. At least a portion of the transdermal delivery device 10, including at least a portion of the transducer 14, is disposed at the grasping region 44 of the face 56. Additionally, the power button 40 is accessible at the face 56.

The housing 42 includes a slot 60 through which the member 16 is inserted and removed. The member 16 can be inserted into the slot 60 at an end 62 of the housing 42 opposite to an end 64 having the interface 28. Alternatively, the slot 60 can receive the member 16 at edges 66 adjacent to the end 64.

When inserted, an interior portion 68 of the member 16 is exposed for contact with the end user while a peripheral portion 70 is retained by the retaining member 18. The interface 22 includes a pair of electrodes 72 which couple to electrodes 74 of the identifier device 20 when the member 16 is inserted. The member 16 covers at least a portion of the transducer 14, and preferably all of the transducer 14, when inserted. Although illustrated to be rectangular, it is noted that the member 16 can be alternatively shaped.

To use the apparatus, the end user inserts the member 16 through the slot 60 and depresses the power button 40. These steps can be performed by the end user in response to a visual alert 76 displayed by the display device 34. The visual alert 76 includes an icon 78 corresponding to the icon 36 viewable on the member 16. The icons 78 and 36 assist the end user in determining which member has the appropriate transdermally-deliverable substance.

Thereafter, the end user contacts the interior portion 68 of the member 16 to transdermally receive a substance. Preferably, the end user applies a finger or a thumb to the member 16. In these cases, the apparatus can be supported by a member such as a table top or a wall. Alternatively, the apparatus is grasped by applying a thumb to the member 16 and one or more fingers to an opposite surface of the housing 42. In general, any portion of the end user's body can be applied to the member 16.

The transdermal delivery device 14 facilitates the permeation of the substance through the end user's skin at the grasping region 44. Once delivered, the member 16 can be removed through the slot 60, or can be retained with the apparatus for a subsequent delivery.

Figure 3:
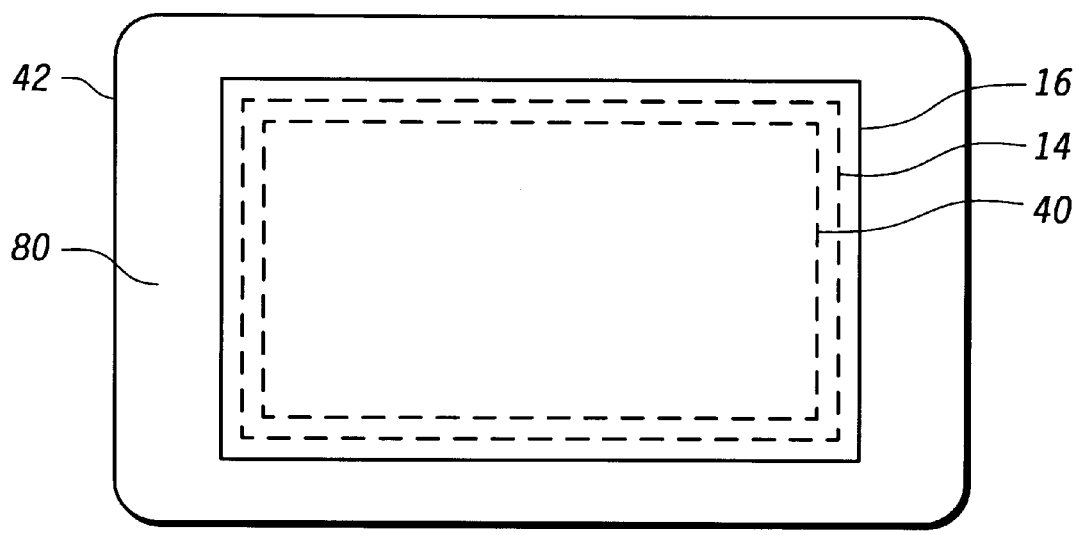
FIG. 3 is a view of a second embodiment of a transdermal delivery apparatus in accordance with the present invention.

FIG. 3 is a view of a second embodiment of a transdermal delivery apparatus in accordance with the present invention. In this embodiment, the housing 42 includes a card-shaped substrate. The card-shaped substrate supports the transdermal delivery device 10 and the member 16 at a first side 80. The transducer 14 of the transdermal delivery device 10 is sandwiched between the member 16 and the substrate. The card-shaped substrate can be rigid, semi-rigid, or resilient.

The power button 40 is co-located with the transducer 14 and the member 16 to activate the apparatus when the member 16 is depressed by a portion of the end user's body. Preferably, the power button 34 is located beneath the member 16 and the transducer 14.

Figure 4:
FIG. 4 is a view of an opposite side of the transdermal delivery apparatus of FIG. 3

FIG. 4 is a view of an opposite side 82 of the transdermal delivery apparatus of FIG. 3. The display device 34 is viewable from the opposite side 82. Preferably, the card-shaped substrate comprises a smart card having the display device 34, the processor 24 and the power source 38 integrated therewith.

In use, the first side 80 of the apparatus is applied to a portion of the end user's body such as his/her arm or hand. While applied, the display device 34 at the opposite side 82 is viewable by the end user. The end user applies the apparatus with a sufficient force to generate a user-initiated activation signal for the power button 40. In response to the user-initiated activation signal, the transdermal delivery device 14 is activated to facilitate the permeation of the substance through the end user's skin.

Once the desired dosage of the substance is delivered, the display device 34 displays an indication that the delivery has completed. Thereafter, the apparatus can be disposed or can be retained for a subsequent use.

Figure 5:
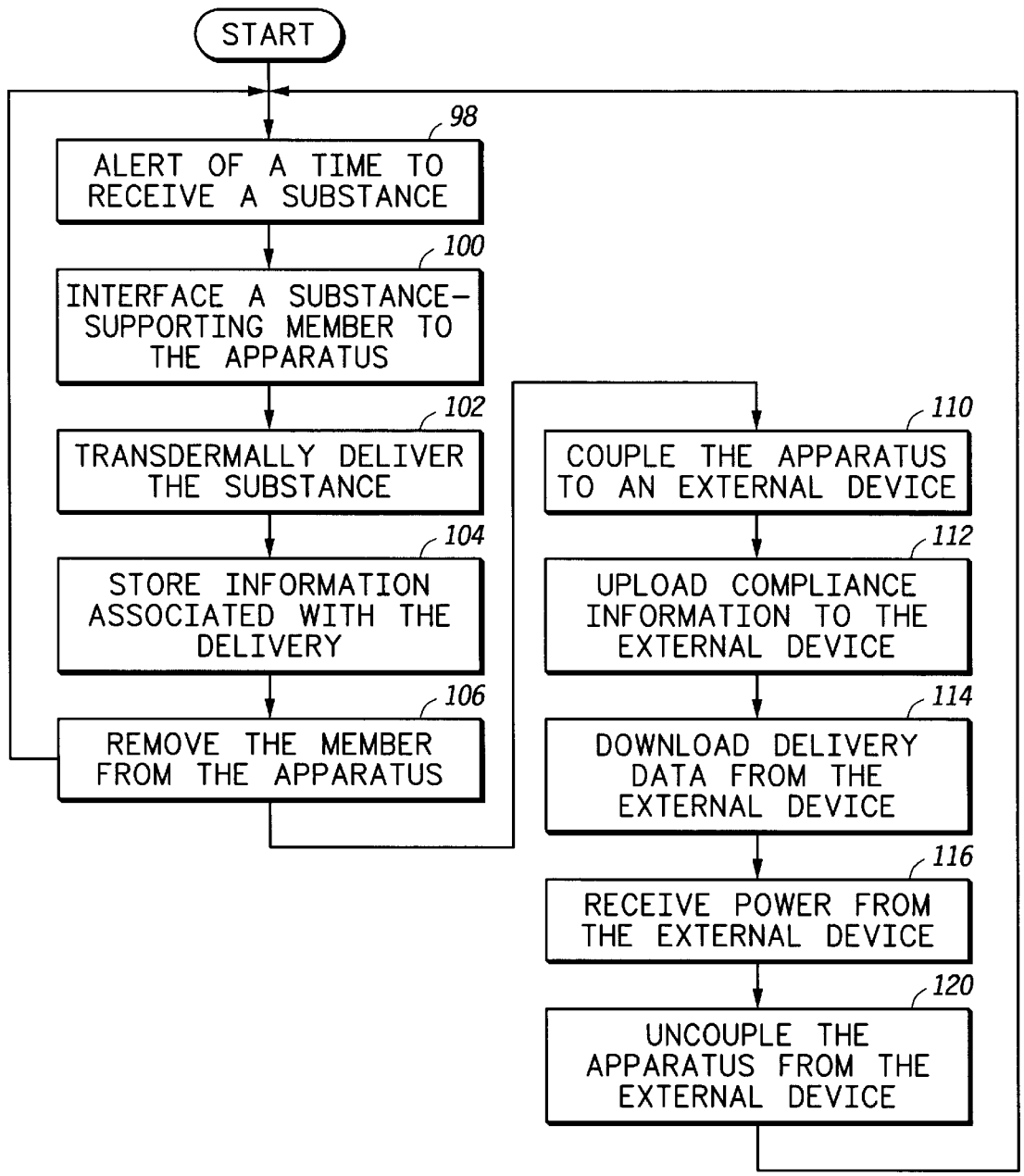
FIG. 5 is a flow chart of a method of using a transdermal delivery apparatus in accordance with the present invention.

FIG. 5 is a flow chart of a method of using a transdermal delivery device in accordance with the present invention. As indicated by block 98, the method includes a step of alerting an end user of a time to receive a substance. This step can include displaying textual and/or graphical information identifying the substance, as described earlier.

As indicated by block 100, if the member 16 is removable, the method optionally includes a step of interfacing the member 16 to the remainder of the apparatus. The member 16 is selected in dependence upon which substance is to be delivered to the end user. The end user can identify the appropriate member based upon information displayed in the step indicated by block 98.

As indicated by block 102, the method includes a step of transdermally delivering the substance using the apparatus. Preferably, the substance is transdermally delivered as described with reference to FIGS. 1 to 4.

As indicated by block 104, the method optionally includes a step of storing information to the memory 26. The information can include compliance data or noncompliance data as described earlier.

As indicated by block 106, the method optionally includes a step of removing the member 16 from the remainder of the apparatus. In this case, the member 16 can be disposed after a single use or after a limited number of uses.

Flow of the method can return back to block 98 to perform one or more subsequent transdermal deliveries. Thereafter, flow of the method proceeds to block 110 which indicates a step of coupling the apparatus to the external device 32. The step of coupling can include coupling the interface 28 and the external device 32 by a wireline connection. For example, the step of coupling can include inserting the PCMCIA card embodiment of FIG. 2 into a PCMCIA socket associated with the external device 32. Alternatively, the step of coupling can include coupling the interface 28 and the external device 32 by a wireless link. The wireless link can include an infrared link or a radio frequency link.

As indicated by block 112, the method optionally includes a step of uploading compliance data and/or noncompliance data from the apparatus to the external device 32. The data is retrieved from the memory 26 by the processor 24, and communicated to the interface 28. A signal representative of the data is communicated from the interface 28 to the external device 32.

As indicated by block 114, the method optionally includes a step of downloading delivery data from the external device 32 to the apparatus. The delivery data directs the operation of the apparatus in transdermally delivering substances. The interface 28 receives a signal representative of the delivery data from the external device 32. The interface 28 communicates the delivery data to the processor 24. The processor 24 stores the delivery data in the memory 26.

As indicated by block 116, the method optionally includes a step of powering the apparatus while the apparatus is linked to the external device 32. This step can include recharging the power source 38 by a current received via the interface 28.

As indicated by block 120, the method optionally includes a step of uncoupling the apparatus from the external device 32. The step of uncoupling can include uncoupling a wireline connection between the interface 28 and the external device 32. For example, the PCMCIA card embodiment of FIG. 2 can be removed from a PCMCIA socket associated with the external device 32.

Flow of the method is directed back to block 98 to perform one or more subsequent deliveries. The subsequent deliveries can be performed in accordance with the delivery data downloaded in the step indicated by block 114. The programmability of the apparatus advantageously allows a plurality of different substances to be delivered using a single apparatus.

FIG. 6 is a view of a first alternative configuration of the transducer 14 and the member 16 for embodiments of the present invention. In this configuration, the member 16 is adjacent a side 130 of the transducer 14. Preferably, the member 16 and the transducer 14 are oriented to be substantially coplanar.

FIG. 7 is a view of a second alternative configuration of the transducer 14 and the member 16 for embodiments of the present invention. In this configuration, the member 16 masks at least a portion of the transducer 14. In particular, the member 16 masks all of the transducer 14 but a plurality of holes. A representative one of the holes is indicated by reference numeral 132. The holes provide paths for directly exposing portions of the end user's body to the transdermal delivery device 10. Preferably, the holes provide paths for directly applying ultrasonic signals to portions of the end user's body.

FIG. 8 is a view of a third alternative configuration of the transducer 14 and the member 16 for embodiments of the present invention. In this configuration, the member 16 includes a plurality of members, a representative one of the members being indicated by reference numeral 134. The members mask portions of the transducer 14. By not masking all of the transducer 14, the transdermal delivery device 10 can directly access portions of the end user's body.

Thus, there has been described herein several embodiments including preferred embodiments of a transdermal delivery apparatus.

Because various embodiments of the present invention transdermally deliver a substance to a hand at a grasping region, they provide a significant improvement in delivering the substance while the end user is holding the apparatus.

Additionally, by supporting a transdermal delivery device with a card-shaped housing, embodiments of the apparatus can be carried in a pocket, purse, or wallet of an end user. A PCMCIA card housing with a PCMCIA connector further facilitates interfacing the apparatus with an external device having a PCMCIA socket. A smart card housing with a smart card connector facilitates interfacing the apparatus with an external device having a smart card interface.

Further, by receiving a removable substance-supporting module, modules can be disposed and replaced after a single-use or a limited number of uses. Also, the transdermal delivery apparatus can deliver any of a variety of substances based upon which module is installed. Delivery data which dictates the delivery can be downloaded from an external device. Still further, by uploading compliance information from the apparatus to an external device, the external device can process, communicate, and/or archive the compliance information.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. An apparatus comprising:
    a PCMCIA card housing; and
    a transdermal delivery device supported by the PCMCIA card housing.

2. The apparatus of claim 1 further comprising a member in communication with at least a portion of the transdermal delivery device, the member supporting a transdermally-deliverable substance.

3. The apparatus of claim 2 wherein the member covers at least a portion of the transdermal delivery device.

4. The apparatus of claim 2 wherein the member includes a pad.

5. The apparatus of claim 2 wherein the transdermally-deliverable substance includes at least one of a pharmaceutical material, a protein, and a hormone.

6. The apparatus of claim 1 wherein the transdermal delivery device includes an ultrasonic emitter.

7. The apparatus of claim 1 wherein the PCMCIA card housing includes a resilient portion.

8. The apparatus of claim 7 wherein the resilient portion supports at least a portion of the transdermal delivery device.

9. An apparatus comprising:

a transdermal delivery device;

an interface; and a processor to receive substance identification data via the interface and to direct the transdermal delivery device to inhibit transdermal delivery of an inappropriate substance based upon the substance identification data.

10. The apparatus of claim 9 wherein the interface is selected from the group consisting of a PCMCIA interface, a serial interface, a parallel interface, a SCSI interface, an infrared interface, a smart card interface, and a radio frequency transceiver.

11. An apparatus comprising:

a housing having a grasping region; and a transdermal delivery device to transdermally deliver a substance to a hand, finger, or thumb of an end user at the grasping region.

12. The apparatus of claim 11 wherein the transdermal delivery device includes an ultrasonic emitter.

13. The apparatus of claim 11 further comprising a thermoelectric cooling member to draw heat from the substance.

14. The apparatus of claim 9 further comprising:

removable member supporting the inappropriate substance; and an identifier device supported by the removable member, the identifier device to identify the inappropriate substance to the processor.

15. The apparatus of claim 14 further comprising at least one electrode coupled to the processor, the at least one electrode to couple with the identifier device.

16. The apparatus of claim 9 wherein the inappropriate substance includes at least one of a pharmaceutical material, a protein, and a hormone.

17. The apparatus of claim 9 wherein the interface comprises a PCMCIA interface.

18. The apparatus of claim 9 wherein the interface comprises a smart card interface.

19. An apparatus comprising:

a credit-card-like housing; and a transdermal delivery device supported by the credit-card-like housing.

20. The apparatus of claim 19 further comprising a member in communication with at least a portion of the transdermal delivery device, the member supporting a transdermally-deliverable substance.

21. The apparatus of claim 20 wherein the member covers at least a portion of the transdermal delivery device.

22. The apparatus of claim 20 wherein the member includes a pad.

23. The apparatus of claim 20 wherein the transdermally-deliverable substance includes at least one of a pharmaceutical material, a protein, and a hormone.

24. The apparatus of claim 19 wherein the transdermal delivery device includes an ultrasonic emitter.

25. The apparatus of claim 19 wherein the credit-card-like housing includes a resilient portion.

26. The apparatus of claim 25 wherein the resilient portion supports at least a portion of the transdermal delivery device.

* * * * *